(12) United States Patent
Chen et al.

(10) Patent No.: US 8,137,666 B2
(45) Date of Patent: Mar. 20, 2012

(54) NATTOKINASE FOR DEGRADING AND REDUCING AMYLOID FIBRILS—ASSOCIATED WITH ALZHEIMER'S DISEASE, PRION DISEASES AND OTHER AMYLOIDOSES

(75) Inventors: Rita P.-Y. Chen, Taipei (TW); Kung-Ta Lee, Yonghe (TW)

(73) Assignee: Academia Sinica, Taipei (TW)

( * ) Notice: Subject to any disclaimer, the term of this patent is extended or adjusted under 35 U.S.C. 154(b) by 169 days.

(21) Appl. No.: 12/618,451

(22) Filed: Nov. 13, 2009

(65) Prior Publication Data

US 2010/0129294 A1   May 27, 2010

Related U.S. Application Data

(60) Provisional application No. 61/117,096, filed on Nov. 22, 2008.

(51) Int. Cl.
*A61K 38/48* (2006.01)
(52) U.S. Cl. .................................................. 424/94.64
(58) Field of Classification Search ........................ None
See application file for complete search history.

(56) References Cited

U.S. PATENT DOCUMENTS 6,607,758 B2   8/2003   Castillo et al.
2006/0127412 A1 *  6/2006   Kakuo et al. ............. 424/195.16

OTHER PUBLICATIONS

Lipscomb et al. Amyloid-specific fluorophores for the rapid, sensitive in situ detection of prion contamination on surgical instruments. J Gen Virol. Sep. 2007;88(Pt 9):2619-26.*
Hsu et al., (2009) "Amyloid-Degrading Ability of Nattokinase from *Bacillus subtilis* Natto" J. Agric. Food Chem. 57 (2), pp. 503-508.

* cited by examiner

*Primary Examiner* — Daniel E Kolker
*Assistant Examiner* — Gregory S Emch
(74) *Attorney, Agent, or Firm* — Hsiu-Ming Saunders; Intellectual Property Connections, Inc.

(57) ABSTRACT

A method of dissolving or disrupting pre-formed or pre-deposited amyloid fibrils and/or inhibiting amyloid formation, deposition, accumulation, or persistence in Alzheimer's disease, prion diseases and/or other amyloidoses in a mammalian subject is disclosed. In the method a therapeutically effective amount of nattokinase is administered.

10 Claims, 7 Drawing Sheets

NATTOKINASE FOR DEGRADING AND REDUCING AMYLOID FIBRILS—ASSOCIATED WITH ALZHEIMER'S DISEASE, PRION DISEASES AND OTHER AMYLOIDOSES

REFERENCES TO RELATED APPLICATION

The present application claims priority to U.S. Provisional Application Ser. No. 61/117,096, filed Nov. 22, 2008, which is herein incorporated by reference in its entirety.

FIELD OF THE INVENTION

The present invention relates generally to degradation and clearance of amyloid, prion and other protein aggregates, and more specifically to methods for degrading and reducing amyloid fibril formation in therapeutic intervention in treating Alzheimer's disease, prion diseases and other amyloidoses.

BACKGROUND OF THE INVENTION

Natto, a fermented food made from boiled soybeans, has been eaten for more than 1000 years in Asia. The fermentation microbe isolated from natto is the Gram-positive endospore-forming bacterium *Bacillus subtilis* natto (formerly designated *Bacillus* natto). Nattokinase is an extracellular enzyme secreted by *B. subtilis* natto and belongs to the alkaline serine protease family, the catalytic center of which contains three conserved residues, Asp-32, His-64, and Ser-221. It has a molecular mass of 27.7 kDa and an isoelectric point of 8.7. Nattokinase is composed of 275 amino acids, and the gene sequence is homologous to those of other members of the subtilisin family (99.5% homology with subtilisin E, 86% with subtilisin BPN', and 72% with subtilisin Carlsberg). It not only degrades fibrin in thrombi but also cleaves plasminogen activator inhibitor type I.

Nattokinase has greater thrombolytic activity than plasmin, a natural thrombolytic protease in blood, and increases the production of plasmin from plasminogen due to its action on plasminogen activator. These observations, together with the fact that it can be absorbed across the intestinal tract after oral administration and induce fibrinolysis, make nattokinase a potential clot-dissolving agent for the treatment of cardiovascular disease. Dietary supplementation with natto suppresses the intimal thickening of arteries and leads to the lysis of mural thrombi seen after endothelial injury. Other clinically thrombolytic agents, such as urokinase and streptokinase, are costly and unstable in the intestinal tract. The use of oral administration of nattokinase in fibrinolytic therapy for thrombosis and the prevention of atherosclerosis is therefore of interest. Nattokinase is currently used as a nutrient supplement to improve circulation in the body. Although much research has been carried out on nattokinase, there has been no interest in whether it can degrade amyloids, which are also highly insoluble and protease resistant.

SUMMARY OF THE INVENTION

The invention relates to applications of nattokinase. In one aspect, the invention relates to a method of degrading various amyloid fibrils by using nattokinase. Nattokinase can be used to digest amyloids in body because it is an edible enzyme and has been used as a nutrient supplement. In another aspect, the invention relates to a method of removing infectious prion by using Nattokinase. Prion is an infectious agent which leads to various prion diseases. The diseases can be transmitted through dietary, surgery, and blood transfusion. Nattokinase can be used to remove prion from animal feeds, surgical instruments, and blood products, etc.

In one aspect, the invention relates to a method of dissolving or disrupting pre-formed or pre-deposited amyloid fibrils and/or inhibiting amyloid formation, deposition, accumulation, or persistence in Alzheimer's disease, prion diseases and/or other amyloidoses in a mammalian subject. The method comprises the step of administering to the subject a composition comprising a therapeutically effective amount of nattokinase, and the therapeutic amount of nattokinase selected for efficacy in treating Alzheimer's disease, prion diseases and/or other amyloidoses in the subject.

In one embodiment of the invention, the nattokinase is extracted from fermented soybean food.

In another embodiment of the invention, the amyloid fibrils are selected from the group consisting of Aβ amyloid fibrils, prion fibrils, insulin fibrils, transthyretin fibrils, and β-microglobulin fibrils.

In another embodiment of the invention, the amyloid fibrils are selected from the group consisting of Alzheimer's Aβ amyloid fibrils and the misfolded/infectious form of prion protein (PrP$^{Sc}$).

Further in another embodiment of the invention, the amyloid fibrils are selected from the group consisting of transthyretin, β2-microglobulin, IAPP (Amylin), and beta amyloid.

In another embodiment of the invention, the therapeutic amount of nattokinase is selected for efficacy in treating Alzheimer's disease.

In another embodiment of the invention, the therapeutic amount of nattokinase is selected for efficacy in treating prion disease.

In another embodiment of the invention, the therapeutic amount of nattokinase is selected for efficacy in treating other amyloidoses selected from the group consisting of familial amyloid polyneuropathy, dialysis related amyloidosis, type 2 diabetes mellitus, and cerebral amyloid angiopathy.

The therapeutically effective amount of nattokinase may be administered orally, by aerosol spray, or in a parenterally injectable or infusible form.

In another aspect, the invention relates to a method of dissolving or disrupting pre-formed or pre-deposited amyloid fibrils and/or inhibiting amyloid formation, deposition, accumulation, or persistence in an in vitro amyloid environment. The method comprises adding to the in vitro environment a composition comprising an effective amount of nattokinase, and the effective amount of nattokinase selected for efficacy in treating amyloid.

In one embodiment of the invention, the amyloid is associated with Alzheimer's disease and/or prion diseases.

In one embodiment of the invention, the in vitro environment comprises an object selected from the group consisting of a medical device, a pharmaceutical product, and an animal feed. The medical device may be selected from the group consisting of a surgical instrument and a hemodialysis tubing.

In one embodiment of the invention, the pharmaceutical product is a blood product.

In another aspect, the invention relates to a method of catalyzing the degradation of amyloid fibrils. The method comprises the step of contacting amyloid fibrils with a composition comprising nattokinase in an amount effective to degrade the amyloid fibrils.

In one embodiment of the invention, the method further comprises the step of administering the composition to a mammalian subject in need thereof prior to the contacting step.

In another embodiment of the invention, the contacting step is performed in an in vitro environment on an object susceptible to contamination by prion protein. The object may be selected from the group consisting of a medical device, a pharmaceutical product, and an animal feed. The in vitro environment may comprise amyloid fibrils selected from the group consisting of Aβ amyloid fibrils, prion fibrils, insulin fibrils, transthyretin fibrils, β-microglobulin fibrils, and any combination thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "amyloid" means insoluble fibrous protein aggregates sharing specific structural traits. Abnormal accumulation of amyloid in organs may lead to amyloidosis, and may play a role in various neurodegenerative diseases. Amyloid deposits are a deposition of proteinaceous mass.

The terms "amyloid β," "amyloid beta (Aβ or Abeta)," and "A beta amyloid" are interchangeable.

The term "a prion" means an infectious agent that is composed primarily of protein. To date, all such agents that have been discovered propagate by transmitting a mis-folded protein state; the protein itself does not self-replicate and the process is dependent on the presence of the polypeptide in the host organism. The mis-folded form of the prion protein has been implicated in a number of diseases in a variety of mammals, including bovine spongiform encephalopathy (BSE, also known as "mad cow disease") in cattle and Creutzfeldt-Jakob disease (CJD) in humans. All known prion diseases affect the structure of the brain or other neural tissue, and all are currently untreatable and are always fatal. In general usage, prion refers to the theoretical unit of infection. In scientific notation, $PrP^C$ refers to the endogenous form of prion protein (PrP), which is found in a multitude of tissues, while $PrP^{Sc}$ refers to the misfolded form of PrP, that is responsible for the formation of amyloid plaques and neurodegeneration.

Amyloid and Amyloidosis

Amyloid is a generic term referring to a group of diverse, but specific extracellular protein deposits which all have common morphological properties, staining characteristics, and x-ray diffraction spectra. Regardless of the nature of the amyloid protein deposited all amyloids have the following characteristics: 1) an amorphous appearance at the light microscopic level and appear eosinophilic using hematoxylin and eosin stains, 2) all stain with Congo red and demonstrate a red/green birefringence as viewed under polarized light, 3) all contain a predominant beta-pleated sheet secondary structure, and 4) ultrastructurally amyloid usually consist of non-branching fibrils of indefinite length and with a diameter of 7-10 nm.

Amyloid today is classified according to the specific amyloid protein deposited. The amyloid diseases include, but are not limited to, the amyloid associated with Alzheimer's disease, Down's syndrome and Hereditary cerebral hemorrhage with amyloidosis of the Dutch type (wherein the specific amyloid is referred to as β-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $\beta_2$-microglobulin amyloid), the amyloid associated with senile cardiac amyloid and Familial Amyloidotic Polyneuropathy (wherein the specific amyloid is referred to as prealbumin or transthyretin amyloid), the amyloid associated with endocrine tumors such as medullary carcinoma of the thyroid (wherein the specific amyloid is referred to as variants of procalcitonin), and systemic amyloidoses. See V. N. Uversky and A. L. Fink (2004) "Conformational constraints for amyloid fibrillation: the importance of being unfolded" *Biochimica et Biophysica Acta,* 1968, 131-153, which is herein incorporated by reference in its entirety.

Although amyloid deposits in clinical conditions share common physical properties relating to the presence of a β-pleated sheet conformation, it is now clear that many different chemical types exist and additional ones are likely to be described in the future. It is currently thought that there are several common pathogenetic mechanisms that may be operating in amyloidosis in general. In many cases, a circulating precursor protein may result from overproduction of either intact or aberrant molecules (ex. plasma cell dyscrasias), reduced degradation or excretion (serum amyloid A in some secondary amyloid syndromes and $\beta_2$-microglobulin in long-term hemodialysis), or genetic abnormalities associated with variant proteins (ex. familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Systemic amyloids which include the amyloid associated with chronic inflammation, various forms of malignancy and Familial Mediterranean Fever (i.e. AA amyloid or inflammation-associated amyloidosis), and the amyloid associated with multiple myeloma and other B-cell dyscrasias (i.e., AL amyloid), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs. For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3-5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes; the $\beta_2$-microglobulin amyloid deposits in the medial nerve leading to carpal tunnel syndrome as observed in patients undergoing long-term hemodialysis; the prealbumin/transthyretin amyloid observed in the hearts of patients with senile cardiac amyloid; and the prealbumin/transthyretin amyloid observed in peripheral nerves of patients who have Familial Amyloid Polyneuropathy.

Table 1 shows a list of diseases that feature amyloid deposition, which includes Alzheimer's disease, prion diseases, Huntington disease, AA amyloidosis, pancreatic islet amyloidosis, hereditary systemic amyloidosis, familial amyloidosis, senile systemic amyloidosis, Pick's disease, AL amyloidosis, Parkinson's disease, diffuse Lewy body disease, atrial amyloidosis, injection-localized amyloidosis, and etc. Proteins which might form amyloid include, but not limited to, prion proteins, Aβ peptides, Cystatin C, Huntingtin, androgen receptor protein, Ataxin-1, serum amyloid A, IAPP, calcitonin, lysozyme, gelsolin, transthyretin, apolipoprotein A1, β-2-microglobulin, immunoglobulin light chain variable domain, alpha-synuclein, fibrinogen, atrial natriuretic factor, insulin, and etc.

TABLE 1

| Disease | Protein Featured |
|---|---|
| Alzheimer's disease | Beta amyloid |
| Type 2 diabetes mellitus | IAPP (Amylin) |
| Parkinson's disease | Alpha-synuclein |
| Transmissible spongiform encephalopathy e.g. Bovine Spongiform Encephalopathy aka "Mad Cow Disease" | Prion |
| Huntington's Disease | Huntingtin |
| Medullary carcinoma of the thyroid | Calcitonin |
| Cardiac arrhythmias | Atrial natriuretic factor |
| Atherosclerosis | Apolipoprotein AI |
| Rheumatoid arthritis | Serum amyloid A |
| Aortic medial amyloid | Medin |
| Prolactinomas | Prolactin |
| Familial amyloid polyneuropathy | Transthyretin |
| Hereditary non-neuropathic systemic amyloidosis | Lysozyme |
| Dialysis related amyloidosis | β2-Microglobulin |
| Finnish amyloidosis | Gelsolin |
| Lattice corneal dystrophy | Keratoepithelin |
| Cerebral amyloid angiopathy | Beta amyloid |
| Cerebral amyloid angiopathy (Icelandic type) | Cystatin |

Alzheimer's Disease and the Aging Population

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid as a major causative factor of Alzheimer's disease pathogenesis. A variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic"

amyloid diseases, there is currently no cure or effective treatment, and the patient usually dies within 3 to 10 years from disease onset (See U.S. Pat. No. 6,607,758 B2, which is herein incorporated by reference in its entirety).

New compounds or agents for therapeutic regimes to arrest or reverse amyloid formation, deposition, accumulation and/or persistence that occurs in Alzheimer's disease and other amyloidoses are therefore desperately needed.

Amyloid as a Therapeutic Target for Alzheimer's Disease

Alzheimer's disease is characterized by the deposition and accumulation of a 39-43 amino acid peptide termed the β-amyloid protein, Aβ or β/A4. Aβ is derived from larger precursor proteins termed β-amyloid precursor proteins (APP or β-APP) of which there are several alternatively spliced variants. The most abundant forms of the βPPs include proteins consisting of 695, 751 and 770 amino acids.

The small Aβ peptide is a major component which makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm. The pathological hallmarks of Alzheimer's disease is therefore the presence of "plaques" and "tangles", with amyloid being deposited in the central core of plaques. The other major type of lesion found in the Alzheimer's disease brain is the accumulation of amyloid in the walls of blood vessels, both within the brain parenchyma and in the walls of meningeal vessels which lie outside the brain. The amyloid deposits localized to the walls of blood vessels are referred to as cerebrovascular amyloid or congophilic angiopathy.

For many years there has been an ongoing scientific debate as to the importance of "amyloid" in Alzheimer's disease and whether the "plaques" and "tangles" characteristic of this disease, were a cause or merely the consequences of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time. Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus and induces nerve cell death in transgenic mice. Injection of the Alzheimer's Aβ into rat brain also causes memory impairment and neuronal dysfunction.

Probably, the most convincing evidence that Aβ amyloid is directly involved in the pathogenesis of Alzheimer's disease comes from genetic studies. It has been discovered that the production of Aβ can result from mutations in the gene encoding, its precursor, beta-amyloid precursor protein. The identification of mutations in the beta-amyloid precursor protein gene which causes early onset familial Alzheimer's disease is the strongest argument that amyloid is central to the pathogenetic process underlying this disease. Four reported disease-causing mutations have now been discovered which demonstrate the importance of Aβ in causing familial Alzheimer's disease. All of these studies suggest that providing a drug to reduce, eliminate or prevent fibrillar Aβ formation, deposition, accumulation and/or persistence in the brains of human patients is believed to serve as an effective therapeutic (See U.S. Pat. No. 6,607,758 B2).

Experiments were conducted to test the ability of nattokinase to degrade amyloid fibrils formed from five different proteins and peptides. The first sample was Aβ40 fibrils because amyloid plaque formation is one of the pathological characteristics of Alzheimer's disease and Aβ40 is one of the major cleaved products of human amyloid precursor protein and the major component of amyloid plaques. The second sample was insulin fibrils as repetitive insulin injection of diabetes patients can cause injection-localized amyloidosis. The third sample was prion peptide fibrils as prion is the agent that is responsible for prion diseases. The prion peptide that corresponded to human prion sequence (108-144) was synthesized to produce amyloid fibrils as previous observations have shown that it is the most likely segment to form an amyloid structure. Human prion protein has either Met or Val at the position 129. The Val-containing sequence was chosen because the resulting amyloid fibrils gave a stronger fluorescence signal with the test agent thioflavin T (ThT) (Hsu et al., (2009) "Amyloid-Degrading Ability of Nattokinase from *Bacillus subtilis* Natto" *J. Agric. Food Chem.* 57 (2), pp 503-508, which is herein incorporated by reference in its entirety.) The fourth and fifth are transthyretin and β2-microglobulin.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Production and purification of nattokinase. *Bacillus subtilis* natto was isolated from a commercial product and maintained on an NB slant at 4° C. Production of nattokinase was performed in a 7-liter fermentor (Bioflo 110 Modular Benchtop Fermentor, New Brunswick Scientific, NJ, USA) based on a method described previously. The fermentation parameters were as follows: working volume 5 liters of 5% (w/v) soymilk (250 g of soybean powder in 5 liters of $H_2O$), aeration rate 1.0 volume per volume per minute, agitation speed 800 rpm and temperature at 37° C. All subsequent steps were at 4° C. After 28 h, the supernatant was recovered by centrifugation at 12,000 g and concentrated on an Amicon Ultra membrane with a 10 kDa cutoff. The concentrated enzyme solution was applied to a gel filtration column (2.6×60 cm) packed with 320 mL of HiPrep 26/60 Sephacryl S-100 high resolution gel (Amersham Biosci.) with a mobile phase of 50 mM sodium phosphate and 150 mM NaCl, pH 7.0 and at a flow rate of 0.5 mL/min. One milliliter fractions were collected, and those with nattokinase activity and showing a single band on 15% SDS-PAGE were pooled. Nattokinase activity was determined by a chromogenic method using S2251 (H-D-Val-Leu-Lys-pNA; Sigma) as the substrate.

Peptide synthesis. Peptide Aβ40 (DAEFRHDSGYEVHHQKLVFFAEDVGSNKGAIIGLMVGGVV; SEQ ID NO: 1) and human prion peptide sequence 108-144 with Val at residue 129 (abbreviated as huPrP) (Ac-NMKHMAGAAAAGAVVGGLGGYVLGSAMSRPIIHFGSD-$NH_2$; SEQ ID NO: 2) were synthesized by the Fmoc-polyamide method on a PS3 peptide synthesizer (Rainin). The N-terminus of the huPrP peptide was acetylated (Ac-) and the C-terminus amidated (—$NH_2$) in order to mimic the configuration in the full-length protein. Preloaded Fmoc-Val-Wang resin (substitution 0.47 mmol/g) was purchased from Anaspec Inc. and used in the synthesis of Aβ40. Rink Amide AM resin (substitution 0.74 mmol/g) was purchased from Novabiochem and used in the synthesis of huPrP. Fmoc-amino-acid derivatives (0.4 mmol) were coupled to 0.1 mmol of resin using 0.4 mmol of benzotriazole-1-yl-oxy-tris-pyrrolidino-phosphonium hexafluorophosphate in dimethylformamide (DMF) containing 4.45% (v/v) of N-methyl morpholine. Acetylation of the N-terminal of huPrP was performed using 0.4 mmol of acetic anhydride instead of amino-acid derivative in the synthetic procedure. Fmoc cleavage was performed using 20% (v/v) piperidine in DMF. The peptides were cleaved from the resin by stirring at room temperature for 1-2 hr with a mixture of 9.4 mL of trifluoroacetic acid, 0.1 mL of triisopropylsilane, 0.25 ml of water and 0.25 ml of ethanedithiol, precipitated with three volumes of ice-cold methyl t-butyl ether, and centrifuged at 2000 g for 10 minutes at 4° C. The pellet was washed another two times with methyl t-butyl ether and dried under vacuum. The resulting white powder was purified by reverse-phase HPLC using a Vydac C18 column (10 mm×250 mm) and an acetonitrile-water mixture containing 0.1% trifluoroacetic acid (v/v). The final products were analyzed by a matrix-assisted laser desorption ionization (MALDI) mass spectrometer. Fractions containing the desired products were lyophilized and stored at −20° C.

Preparation of amyloid fibrils. For Aβ40 fibril formation, a 500 μM Aβ40 stock solution was prepared in 75% trifluoroethanol. The peptide concentration was quantified by the absorbance at 275 nm. To form fibrils, the stock solution was diluted to 25 μM in 20 mM sodium phosphate buffer, 150 mM KCl, pH 7, and incubated at 25° C. for about two weeks. The huPrP fibrils were prepared by dissolving the huPrP peptide in 20 mM NaOAc, 140 mM NaCl, pH 3.7 to a final concentration of 50 μM, and incubating the solution at 25° C. for about one week. To obtain insulin fibrils, bovine insulin (Sigma) was dissolved in dilute HCl (pH 2.1) at a concentration of 2.5 mg/mL, and incubated at 60° C. for about two days.

Human transthyretin (TTR) from plasma and human β2-microglobulin (β2-M) from urine were bought from Sigma. For TTR to form fibrils, 4 mg/ml of TTR was first dissolved in pH 7.4 buffer (10 mM phosphate, 100 mM KCl, 1mM EDTA), then diluted to 0.2 mg/ml with pH 4.4 buffer (50 mM NaOAc, 100 mM KCl) and incubated at 37° C. for 3 days. β2-M fibrils were prepared by dissolving β2-M in pH 2.5 buffer (25 mM NaOAc, 25 mM phosphate, 0.05% NaN$_3$) to the concentration of 84 μM and incubated at 37° C. with agitation at 250 rpm for 1 day.

Fibril formation was monitored by the appearance of negative ellipticity at 218 nm using circular dichroism spectroscopy, or fluorescence emission on binding ThT using fluorescence spectroscopy.

Circular dichroism (CD) spectroscopy. Each sample was placed in a 1-mm quartz cell and the CD spectrum between 200 and 250 nm recorded on a J-715 CD spectrometer (JASCO, Japan). The bandwidth was set at 2 nm and the step resolution was 0.05 nm. Two scans were averaged for each sample.

Thioflavin T binding assay. Thioflavin T (ThT) binding assay measures the fluorescence intensity change in ThT on binding to amyloid fibrils. Thioflavin T fluorometry has been extensively used for identifying the presence of amyloid fibrils. Thioflavin T is known to bind to fibrillar amyloid proteins, and a decrease or increase in fluorescence was previously shown to correlate with a decrease or increase in the amount of amyloid fibrils. The Alzheimer's Aβ (1-40) protein when incubated at 37° C. tends to spontaneously form amyloid fibrils which increase in quantity over time. In Alzheimer's disease and other amyloidoses, amyloid fibril growth is believed to involve amyloid protein self-interactions (i.e., Aβ-Aβ interactions).

A stock solution of 5 mM of ThT (Sigma) was prepared by dissolving 2 mg of the dye in 1.25 mL of 100 mM phosphate buffer containing 140 mM NaCl, pH 8.5, and passing the solution through a 0.22 μm Millipore filter. A fresh working solution was prepared by adjusting the final dye concentration to 200 μM. A 30 μL aliquot of the sample was mixed with 30 μL of 200 μM ThT dye solution for 1 min at room temperature, then the fluorescence emission between 460 and 600 nm was measured in a 3-mm path-length rectangular cuvette on a FP-750 spectrofluorometer (JASCO, Japan) with excitation at 442 nm.

Protease solutions. Stock solutions of all proteases (all from Sigma except nattokinase) used in the study were prepared at a concentration of 49 μM and quantified by the Bradford assay (Bio-Rad). The protease solutions were prepared in different buffer according to the manufacturer's instructions. Nattokinase and subtilisin Carlsberg were dissolved in 50 mM phosphate buffer containing 150 mM NaCl, pH 7. Proteinase K was dissolved in 10 mM Tris-HCl buffer, pH 7. Trypsin was dissolved in 1 mM HCl, and human plasmin was dissolved in distilled water. For comparison with other proteases, nattokinase was dissolved in pH 7 buffer. To degrade transthyretin and β2-microglobulin, nattokinase was dissolved in the same buffer but at pH 7.4.

Degradation of different kinds of amyloid fibrils by nattokinase. The prepared Aβ40, huPrP and insulin fibrils fibrils were collected by centrifugation at 14,000 g for 20 min at room temperature and suspended in 50 mM phosphate buffer containing 150 mM NaCl, pH 7. In order to obtain more homogeneous fibrils, the fibril solutions were incubated in an ultrasonic bath for 10 min before use. For enzymatic reaction, 1 μL of nattokinase solution was mixed with 179 μL of each kind of fibril solution (final nattokinase concentration: 0.27 μM) and the mixture incubated for 1 hr at 40° C. Fibril digestion was examined by CD spectroscopy and/or the ThT binding assay. For transthyretin (TTR) and β2-M fibrils, the digestion reaction was done in the physiological condition (pH7.4 and 37° C.). The TTR fibrils were collected by centrifugation at 14,000 g for 20 min at room temperature and suspended in 50 mM phosphate buffer containing 150 mM NaCl, pH 7.4. β2-M fibrils could not be collected by centrifugation. The β2-M fibril solution was diluted 3 fold in 50 mM phosphate buffer, pH7.4 before adding the enzyme.

Effects of Temperature and pH on the Amyloid-Degrading Activity of Nattokinase.

In this experiment, insulin fibrils were used as the substrate for the nattokinase reaction because larger amounts of fibrils were needed. Insulin was commercially available and it took only 2 days to make insulin fibrils. The effect of temperature on nattokinase activity was measured by digestion at pH 7 and various temperatures from 30° C. to 60° C. The degradation of insulin fibrils was monitored using the ThT binding assay. To examine the effect of pH on nattokinase activity, insulin fibrils were suspended in the following buffers: 50 mM NaOAc and 150 mM NaCl (pH 5), 50 mM phosphate and 150 mM NaCl (pH 6 and 7), 50 mM Tris-HCl and 150 mM NaCl (pH 8 and 9), and 50 mM glycine-NaOH and 150 mM NaCl (pH 10). The reaction was carried out at 40° C. Nattokinase activity was measured by CD spectroscopy as the ThT binding assay is pH-sensitive.

Comparison of Aβ fibril-degrading activity of different proteases. The enzymatic reaction was carried out at 37° C. and pH 7 for 1 hr using nattokinase, proteinase K, subtilisin Carlsberg, trypsin or plasmin. The reaction mixture contained 
1 μL of protease stock (49 μM) and 179 μL of Aβ fibril solution, and 30 μL of the mixture was removed every 15 min for testing in the ThT binding assay.

Measurement of rate of Aβ fibril degradation by nattokinase. The Aβ peptide concentration in the fibril form was determined by subtracting the nonaggregated Aβ peptide concentration in the supernatant fraction after centrifugation from the overall Aβ concentration. The fibrils were suspended in 50 mM phosphate buffer containing 150 mM NaCl, pH 7.4. Nattokinase was added into the fibril solution at different enzyme concentrations and the mixture was incubated at 37° C. After different incubation time points, the amount of remaining fibril was measured by the ThT binding assay. The rate of fibril degradation was calculated from the time course of fibril degradation.

Digestion of Scrapie-Infected Hamster Brain

Brain homogenate (10%) of hamster infected with 263K strain of prion (provided by Dr. Caughy's Lab) were diluted to 4% with pH10 glycine/NaOH buffer (50 mM glycine, 150 mM NaCl) and digested with 50 μg/ml of nattokinase at 50° C. The digestion was carried out for 7 hrs, and the reaction was added with additional 25 μg/ml of nattokinase every hour. The initial reaction volume was 100 μL. To assay the effect of degradation, 10 μL of sample was taken out every hour and the reaction was stopped by 1 mM PMSF.

Western Blot and Detection of PrP$^{Sc}$

Figure 1:
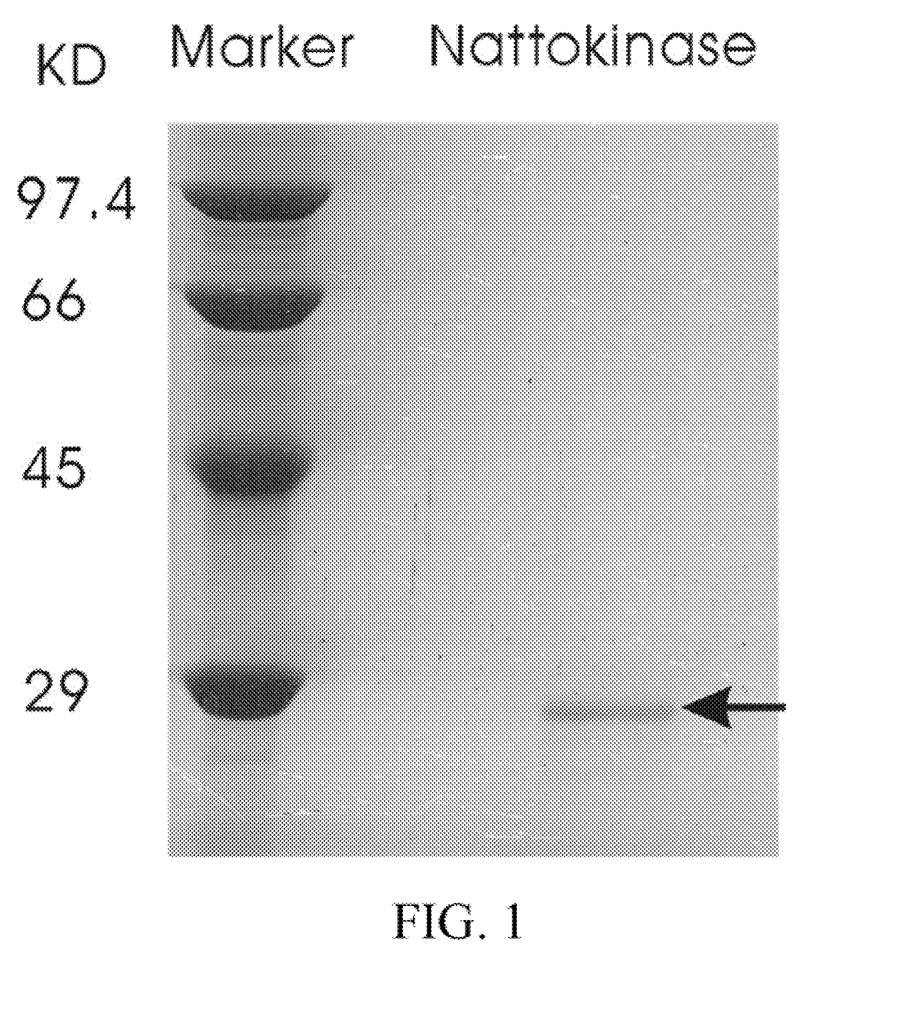
FIG. 1 a photograph of SDS-PAGE gel showing purified nattokinase (indicated by an arrow).
Figure 2:
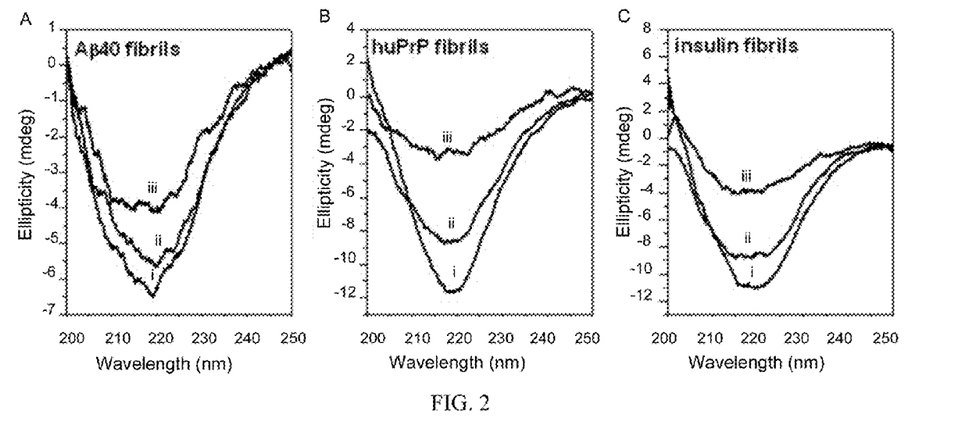
FIGS. 2A-2C are graph displays showing the CD spectra of proteins before and after digestion by nattokinase. The line (i) indicates the spectrum immediately after enzyme addition. The lines (ii) and (iii) indicate the spectra of the samples digested for 1 and 48 h, respectively.
Figure 3:
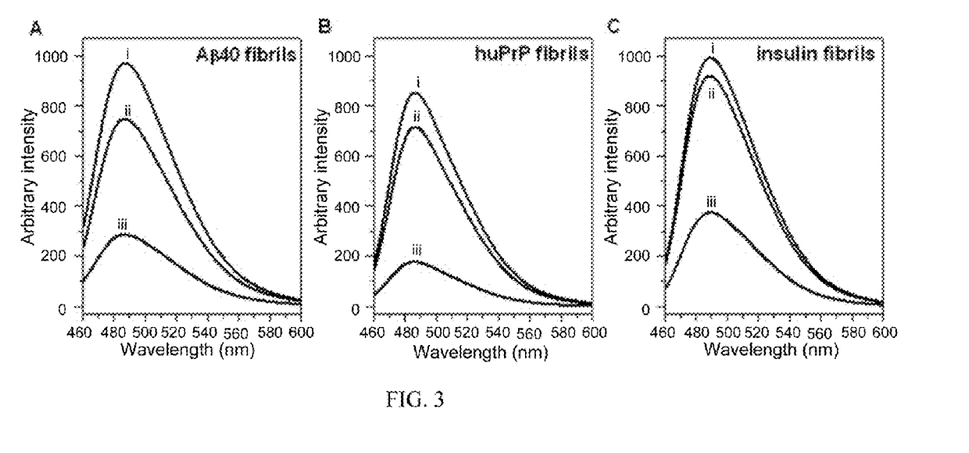
FIGS. 3A-3C are graph displays showing the fluorescence emission spectra of proteins before and after digestion by nattokinase using ThT binding assay. The line (i) indicates the spectrum immediately after enzyme addition. The lines (ii) and (iii) indicate the spectra of the samples digested for 1 and 48 h, respectively.
Figure 4:
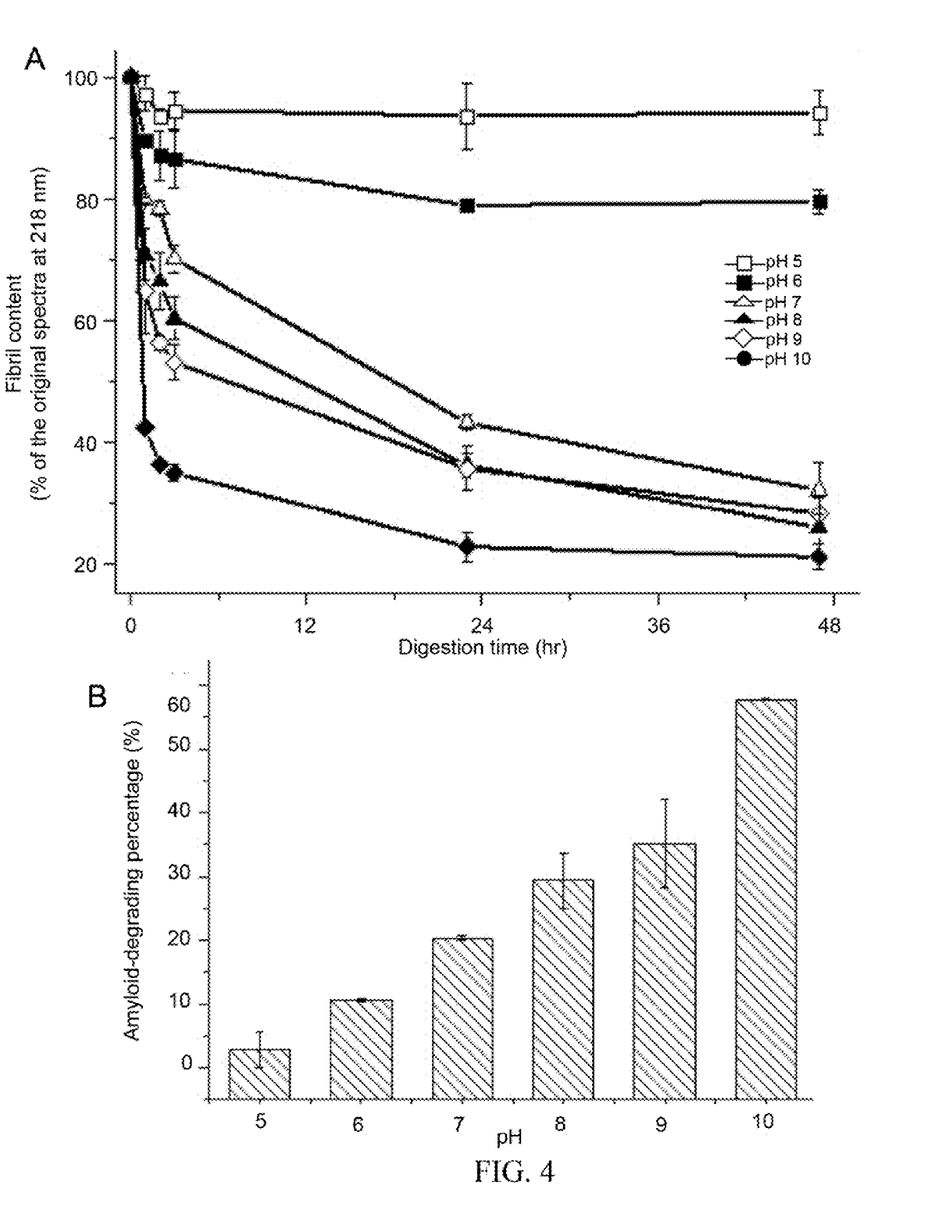
FIGS. 4A-4B are graphs showing the degradation of insulin fibrils by nattokinase at different pH.
Figure 5:
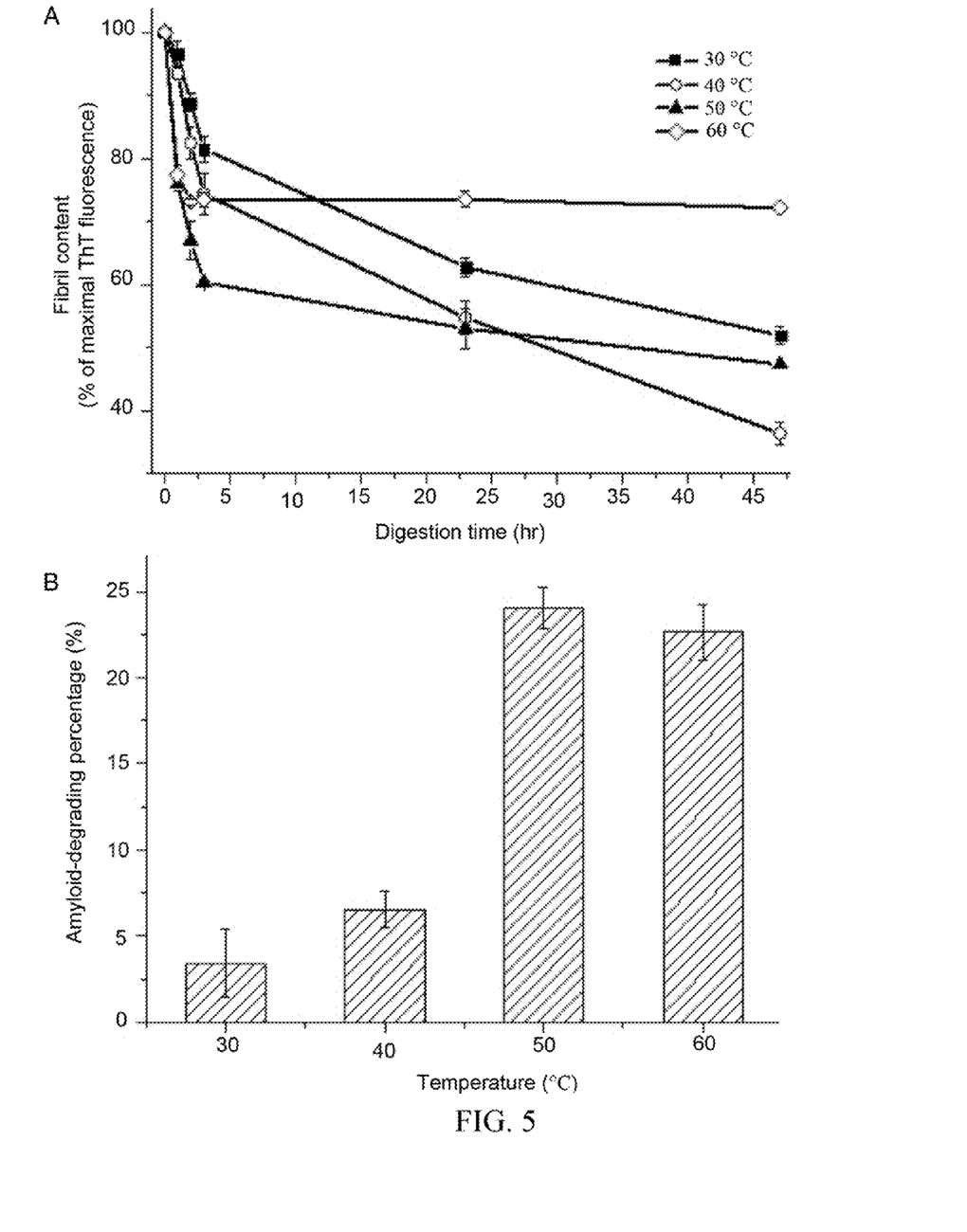
FIGS. 5A-5B are graphs showing the degradation of insulin fibrils by nattokinase at different temperatures.
Figure 6:
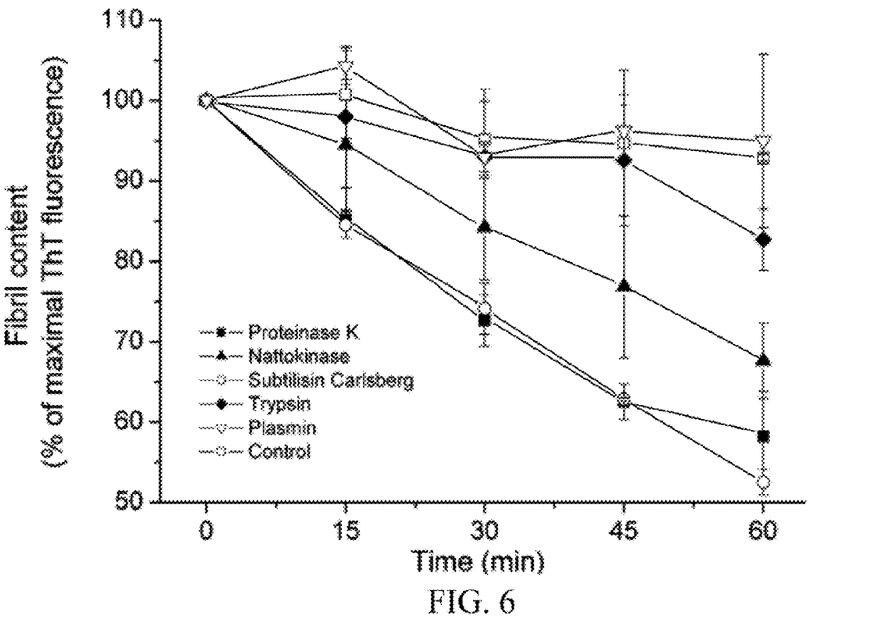
FIG. 6 is a graph comparing Aβ40 fibril degradation by various proteases.

Prior to SDS-PAGE, the digested 263K brain homogenates were boiled at 100° C. for 10 min with sample loading buffer containing 2% SDS and 1% 2-mercaptoethanol. Prion protein (PrP$^{sc}$) was detected with the primary antibody 1E4 (Abcam, raised with synthetic cow prion peptide 108-119) at 0.25 μg/ml and 0.33 μg/ml of goat anti-mouse IgG conjugated with horseradish peroxidase (Perkin Elmer). The signal was recorded on a Fuji medical X-ray film.

Example 1

Nattokinase Degrades and Reduces Amyloid Fibrils Formed from Peptides

Nattokinase was purified from a liquid culture by gel filtration chromatography. Fractions containing nattokinase were identified using the activity assay, then tested for the presence of a 27.7 kDa band on SDS-PAGE. The band was characterized by a N-terminal sequence analysis. Those fractions showing a pure protein were pooled and lyophilized (FIG. 1). FIG. 1 shows a 15% SDS-PAGE of a purified nattokinase, as indicated by the arrow.

To determine whether nattokinase has amyloid-degrading activity, Aβ40 fibrils formed from a synthetic Aβ40 peptide, huPrP fibrils formed from a synthetic human prion peptide (containing human prion protein amino acids 108-144 with valine at residue 129), and insulin fibrils formed from purified bovine insulin were used. At 40° C. and pH 7, nattokinase degraded all three fibrils, as shown by the decrease in the amplitude of the negative ellipticity at 218 nm in the CD spectra after 1 hr of digestion, indicating a loss of β-sheet structure (FIG. 2). In FIG. 2, the spectrum immediately after enzyme addition is shown by the line (i). The spectra of the samples digested for 1 and 48 h are shown by the lines (ii) and (iii), respectively.

Similar results were obtained using the ThT binding assay, in which the decrease in the ThT fluorescence intensity at 487 nm indicated a loss of amyloid structure after nattokinase digestion (FIG. 3). FIG. 3 shows fluorescence emission spectra of Aβ40 fibrils (A), huPrP fibrils (B), and insulin fibrils (C) before and after digestion by nattokinase at 40° C., pH 7, using ThT binding assay. The spectrum immediately after enzyme addition is shown by the line (i). The spectra of samples digested for 1 and 48 h are shown by the lines (ii) and (iii), respectively.

These results demonstrated that nattokinase was able to degrade all three different amyloid fibrils.

The discovery that nattokinase was capable of causing a "dissolution" or "disruption" of pre-formed Alzhemer's disease and prion disease amyloid fibrils is important for any potential anti-amyloid drug which can be used in patients who already have substantial amyloid deposition in organs and/or tissues. For example, Alzheimer's disease patients in mid-to-late stage disease have abundant amyloid deposits in their brains as part of both neuritic plaques and cerebrovascular amyloid deposits. A natural therapeutic agent capable of causing dissolution of pre-existing amyloid would be advantageous for use in these patients.

Example 2

Nattokinase Digests Amyloid in a pH and Temperature-Dependent Manner

The fibrinolytic activity of nattokinase is known to be stable at neutral and alkaline pH (7-12), but labile below pH 5. To examine the effect of pH on the amyloid-degrading activity of nattokinase, we carried out proteolytic digestion of insulin fibrils over a broad range of pH values (pH 5-10) at 40° C. FIG. 4 shows degradation of insulin fibrils by nattokinase at different pHs. The digestion was carried out at 40° C. and monitored by CD spectroscopy. FIG. 4A shows the time-course of degradation monitored by measuring the remaining amyloid fibrils, and FIG. 4B shows percentage of amyloid degradation at different pHs calculated using the data for one hour of digestion. The 100% was defined as the CD ellipticity at 218 nm of the sample before treatment. The values are the mean±SEM for the results of two experiments. The results indicated that the nattokinase activity increased gradually with increasing pH and reached a maximal activity at pH 10 in the range tested. At pH 5, nattokinase did not show any activity.

In addition, it has been reported that the fibrinolytic activity of nattokinase is gradually lost above 60° C. We therefore tested the amyloid-degrading ability of nattokinase at different temperatures and pH 7. FIG. 5 shows degradation of insulin fibrils by nattokinase at different temperatures between 30 and 60° C. The digestion was carried out in phosphate buffer, pH 7, and monitored using the ThT binding assay. FIG. 5A shows the time-course of degradation as monitored by measuring the remaining amyloid fibrils. FIG. 5B shows the percentage of amyloid degradation at different temperatures calculated using the data for one hour of digestion. The 100% was defined as the fluorescence intensity at 487 nm of the sample before treatment. The values are the mean±SEM for the results of two experiments.

As shown in FIG. 5A, at 60° C. insulin fibrils were degraded rapidly in the first few minutes, but then the digestion stopped, probably due to the inactivation or self-digestion of nattokinase. At 50° C. rapid initial digestion was observed, followed by slow digestion, while at 40° C. the initial release was less rapid, but digestion continued and was more complete than in the other cases.

Example 3

Nattokinase is More Effective than Plasmin in Digesting Amyloid

Nattokinase and several other serine proteases were tested for their ability to digest Aβ fibrils at 37° C., pH 7. The proteases used were proteinase K (a keratinolytic enzyme and subtilisin-like serine protease used in research on prion diseases), subtilisin Carlsberg (a subtilisin-like serine protease), trypsin, and plasmin (a fibrinolytic serine protease). FIG. 6 shows the results of the comparison of Aβ40 fibril degradation by proteinase K, nattokinase, subtilisin Carlsberg, trypsin, and plasmin. The digestion was carried out at 37° C., pH 7 and monitored by ThT binding assay every 15 min. The 100% was defined as the fluorescence intensity at 487 nm of the control before incubation.

Figure 7:
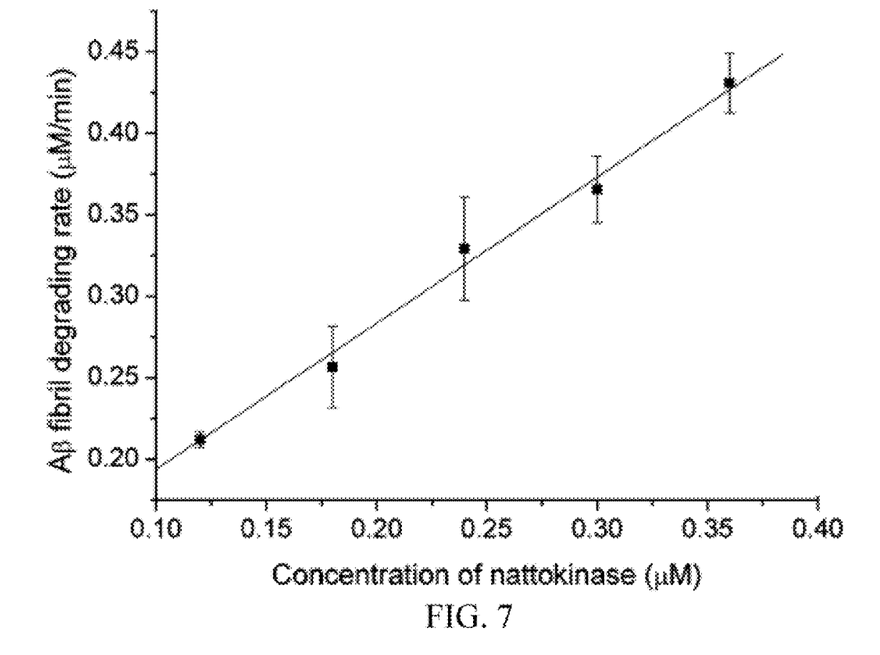
FIG. 7 is a graph showing nattokinase concentration dependence of Aβ40 fibril degradation.

As shown in FIG. 6, at 37° C., pH 7 proteinase K and subtilisin Carlsberg degraded Aβ fibrils at the highest rates. The hydrolysis rate was slower for nattokinase and much slower for trypsin, while plasmin was ineffective. Although the digestion was not performed at the optimal temperature for proteinase K, subtilisin Carlsberg or nattokinase in order to mimic body temperature, the amyloid-degrading activity of these proteases was still much greater than those of trypsin and plasmin. It has been shown that plasmin can degrade Aβ monomer and aggregated Aβ, but the rate (0.003 $s^{-1}$) is 20 times lower than that for degrading aggregated fibrin (0.064 $s^{-1}$) and 160 times lower than that for degrading Aβ monomer (0.48 $s^{-1}$). In our study, under the same reaction conditions, nattokinase was more efficient than plasmin in cleaving amyloid. The rate of Aβ fibril degradation by nattokinase was 0.015 $s^{-1}$ at 37° C., pH 7.4 (FIG. 7). FIG. 7 shows nattokinase concentration dependence of Aβ fibril degradation. Aβ fibril (44 µM) was incubated with nattokinase (final enzyme concentration of 0.12, 0.18, 0.24, 0.30, or 0.36 µM) at 37° C. in phosphate buffer, pH 7.4. The values are the mean±SEM for the results of two separate experiments.

Example 4

Nattokinase Digests Amyloid Fibrils Formed from Purified Human Proteins

Figure 8A:
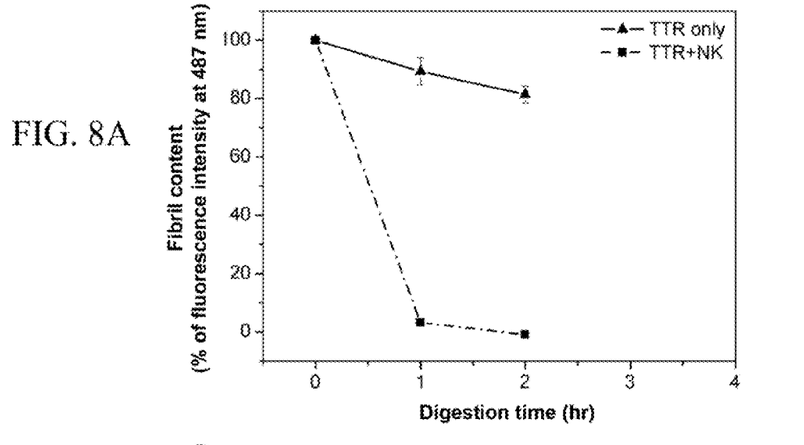
FIG. 8A is a graph showing degradation of TTR fibrils with nattokinase.
Figure 8B:
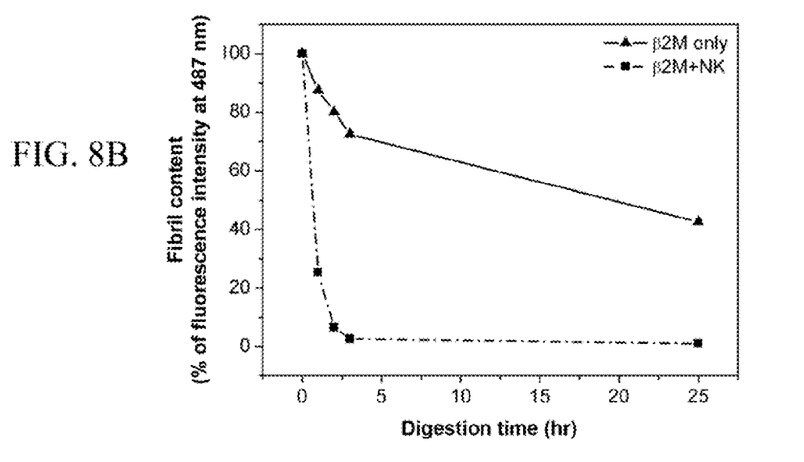
FIG. 8B is a graph showing degradation of β2-microglobulin fibrils with nattokinase.

At the condition of pH 7.4 and 37° C., TTR fibrils were almost completely degraded by nattokinase in one hour. As for β2-M fibrils, it was degraded near completion in two hours (FIG. 8). Though the fluorescence signals for TTR and β2-M fibrils decreased with time, the fibril-degrading capability of nattokinase was significant. FIGS. 8 A-B show degradation of TTR fibrils and β2-M fibrils with nattokinase at pH 7.4 and 37° C. The digestion was monitored by ThT fluorescence emission at 487 nm. The 100% was defined as the fluorescence intensity of the initial fibrils upon ThT binding. The values are the mean±SEM for the results of two experiments.

Example 5

Nattokinase Digests In Vivo Formed Prion

Figure 9:
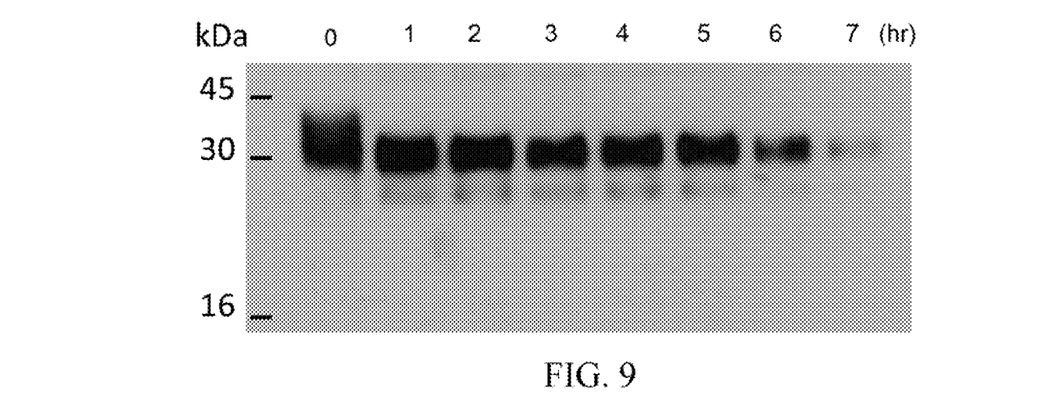
FIG. 9 is a photograph showing a Western blot of the nattokinase-digested 263K-infected brain homogenate. The prion was detected with 1E4 antibody.

The brain homogenate of hamster infected with 263K strain of prion was digested with 50 µg/ml of nattokinase at 50° C., pH 10. Nattokinase works most efficiently at this digestion condition in a short period of time but it is unable to sustain this high degrading efficiency. To completely degrade the prion in the homogenate, we added additional 25 µg/ml of nattokinase every hour after taking some samples for western blot. FIG. 9 shows the results of a Western blot of the nattokinase-digested 263K-infected brain homogenate. The prion was detected with 1E4 antibody. As shown in FIG. 9, the protease-resistant core of the prion (about 30 kDa) was gradually degraded. It was expected that the prion signal would be undetectable with a higher concentration of nattokinase in the digestion.

Discussions

The above experiments used five kinds of in vitro prepared amyloid fibrils including Aβ40 amyloid fibrils, insulin amyloid fibrils, huPrP (comprising prion sequence 108-144) amyloid fibrils, TTR amyloid fibrils, and β2M amyloid fibrils and in vivo formed hamster prion (strain 263K) to test the amyloid-degrading ability of nattokinase. After treatment of those amyloid fibrils with nattokinase, the amyloid amount decreased (FIGS. 2, 3, 8 and 9), indicating the general amyloid-degrading ability of nattokinase.

This amyloid-degrading ability of nattokinase suggests that it may be useful in the treatment of amyloid-related diseases. The feather-degrading enzyme keratinase (Versazyme) produced by *Bacillus licheniformis* can degrade preheated prion and is useful for inactivating prion in meat and bone meal and for decontaminating medical instruments, but cannot be taken orally. Many proteins and peptides including immunoglobin light chain, transthyretin, β2-microglobulin, serum amyloid A protein, Aβ peptides, and insulin can form amyloid deposits in the body. Aβ peptides can move from the brain into the blood with the aid of low density lipoprotein receptor-related protein and p-glycoprotein. In addition, prion diseases can be transmitted through blood transfusion, suggesting the presence of prion in the blood. Amyloid fibrils are insoluble and not easily digested by proteases. The discovery of an enzyme which can be safely taken orally and can degrade amyloid fibrils could be very useful in treating amyloid-related diseases. Nattokinase not only dissolved blood clots, but also degraded amyloid fibrils. Our amyloid-degrading studies demonstrated that it is active at neutral pH and body temperature. Previous results in rats, dogs, and humans have suggested that nattokinase can enter the circulation when taken orally, so it has the potential to clear amyloid deposits in various parts of the body. Moreover, prion diseases can be transmitted by the use of contaminated surgical instruments. Nattokinase can tolerate a temperature of 50° C. and functions even better under basic conditions such as pH 10, suggesting that it might be useful in prion decontamination of instruments (FIG. 9).

In conclusion, Nattokinase is an edible enzyme that has been eaten by humans and animals for several hundred years. It is safe to use nattokinase in humans or any materials which will be used by humans. Nattokinase can be used to digest and remove various amyloid fibrils in the body. It can be used to remove infectious prion proteins from surgical instruments or animal feeds. Nattokinase can also be used to remove prion or amyloid fibrils from blood products and prevent amyloid precipitation on hemodialysis tubing.

Further Aspects and Utilizations of the Invention Therapeutic Applications

Prior to administration in a patient, nattokinase may be formulated in a pharmaceutical composition with one or more pharmaceutical acceptable carriers, diluents or excipients. In one embodiment of the invention, a patient who has Alzheimer's disease, prion disease, type II diabetes or any other amyloidosis, would orally consume commercially available nattokinase in pill, tablet, caplet, soft and hard gelatin capsule, lozenge, vegicap, liquid drop, solution, syrup, tea bag, and/or bark powder form.

In another embodiment nattokinase obtained commercially in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweeting agents or flavoring agents. The composition comprising nattokinase may be formulated so as to provide quick, sustained or delayed response of the active ingredient after administration to the patient. The nattokinase compositions are preferably formulated in a unit dosage form, each dosage containing from about 1 to about 10,000 mg of nattokinase, more usually about 250 or 500 to about 1,000 or 2,000 mg. However, it will be understood that the therapeutic dosage administered will be determined by the physician in the light of the relevant circumstances including the clinical condition to be treated, the organ or tissues affected or suspected to be affected with amyloid accumulation, and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active nattokinase calculated to produce the desired therapeutic effect in association with a suitable pharmaceutical carrier.

The following formulation examples are illustrative only and are not intended to limit the scope of the invention in any way. Hard gelatin capsules may be prepared by using 500 mg of nattokinase, 400 mg of starch, and 20 mg of magnesium stearate. The above ingredients are mixed and filled into hard gelatin capsules in 920 mg quantities.

A tablet is prepared by using 500 mg of nattokinase, 800 mg of microcrystalline cellulose, 20 mg of fumed silicon dioxide and 10 mg of stearic acid. The components are blended and compressed to form tablets each weighing 1230 mg.

An aerosol solution is prepared by using a weight ratio: 0.25 nattokinase, 29.75 ethanol, and 70 of propellent 22 (chlorodifluoromethane). The nattokinase is mixed with ethanol. The mixture is added to a portion of the Propellent 22, cooled to −30° C., and transferred to a filling device. The required amount is then fed to a stainless steel container and diluted with the remainder of the propellent. The value units (listed above) are then fitted to the container. Such an aerosol form of nattokinase may be useful for the treatment of amyloids involving the brain (such as Alzheimer's disease, Down's syndrome, prion diseases etc) by using an aerosol or nasal spray. Previous studies have suggested that in these central nervous system amyloidoses the initial form of entry of a possible environmental agent which may be playing a role in pathogenesis may be derived from the outside world through the nasal passages.

Tablets are made by using 240 mg of nattokinase, 180 mg of starch, 140 mg of microcrystalline cellulose, 16 mg of polyvinylpyrrolidone (as 10% in water), 18 mg of sodium carboxymethyl starch, 2 mg of magnesium stearate and 2 mg of talc (total=600 mg). Nattokinase, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 600 mg.

Capsules each containing 160 mg of medicant are made by using 160 mg of nattokinase, 118 mg of starch, 118 mg of microcrystalline cellulose, and 4 mg of magnesium stearate (total=400 mg). The nattokinase, cellulose, starch and magnesium stearate are blended, passed through a No. 45 mesh U.S. sieve, and filled into hard gelatin capsules in 400 mg quantities.

Suppositories each containing 225 mg of nattokinase are made by using 225 mg of nattokinase, 2,000 mg of saturated fatty acid glycerides (total=2,225 mg). The nattokinase is passed through a No. 60 mesh U.S. sieve and suspended in the saturated fatty acid glycerides previously melted using the minimum heat necessary. The mixture is then poured into a suppository mold of nominal 2 g capacity and allowed to cool.

Suspensions each containing 50 mg of medicant per 5 ml dose are made by using 50 mg of nattokinase, 50 mg of sodium carboxymethyl cellulose, 1.25 ml of syrup, 0.10 ml of benzoic acid solution, flavor, color, and purified water to total 5 ml. The medicant is passed though a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An intravenous formulation is prepared by using 250 mg of nattokinase, and 1000 mg of isotonic saline. The solution of the above ingredients is administered intravenously at a rate of 1 ml per minute to a subject in need of treatment.

In one embodiment of the invention, nattokinase can be administered in any pharmaceutically acceptable vehicle. As used herein "pharmaceutically acceptable vehicle" includes, but is not limited to, any and all solvents, sterile liquids, such as water and oils, including those of petroleum, animal, vegetable or synthetic origin, such as peanut oil, soybean oil, mineral oil, sesame oil and the like, dispersion media, coatings, antibacterial and antifungal agents, isotonic and adsorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Supplementary active compounds can also be incorporated into the compositions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Amyloid formation, deposition, accumulation and/or persistence in a subject is inhibited by administrating nattokinase in a therapeutic dosage to the subject. The term subject is intended to include living organisms in which amyloidosis can occur. Examples of subjects include humans, monkeys, cows, dogs, sheep, cats, mice, rats, and transgenic species thereof. Administration of nattokinase to a subject to be treated can be carried out using known procedures, at dosages and for periods of time effective to inhibit amyloidosis in the subject. An effective amount of nattokinase necessary to achieve a therapeutic effect may vary according to factors such as the amount of amyloid already deposited at the organ or tissue site in the subject, the age, sex and weight of the subject, and the ability of the nattokinase formulation to inhibit amyloid formation, deposition, accumulation, persistence, and/or to cause dissolution of pre-formed amyloid in the subject. Dosage regimens can therefore be adjusted to provide the optimum therapeutic response. For example, several divided doses may be administered daily or the dose may be proportionally reduced as indicated by the needs of the therapeutic situation. A non-limiting example of an effective dose range for nattokinase is between 10 and 1000 mg/kg of body weight/per day, or 10 to 100 mg/kg of body weight.

Different modes of delivery of nattokinase may be used. Accordingly, one route of administration is oral administration. Alternatively, nattokinase may be administered by other suitable routes such as subcutaneous, intravenous, intraperitoneal, all routes administered by injection. Depending on the route of administration, the active compound may be coated in a material to protect nattokinase from the action of acids and other natural conditions which may inactivate nattokinase.

To administer nattokinase, it may be necessary to coat it with, or co-administer it with, a material to prevent its activation. For example, nattokinase may be administered to a subject in an appropriate carrier, for example, liposomes or a diluent. Pharmaceutically acceptable diluents include saline and aqueous buffer solutions. Liposomes include water-in-oil-in-water CGF emulsions as well as conventional liposomes.

The nattokinase may also be administered parenterally or intraperitoneally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions or dispersions and sterile powders for the preparation of sterile injectable solutions or dispersion. In all cases, the composition must be sterile and must be fluid to the extent that easy use in the syringe exists. It must be stable under the conditions of manufacture and storage and must be preserved against the contaminating action of microorganisms such as bacteria and fungi. The vehicle can be a solvent or dispersion medium containing, for example, water, ethanol, polyol (for example glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, prabens, chlorobutanol, phenol, ascorbic acid, thimerosal, and the like. In many cases, it will be preferable to include isotonic agents, for example, sugars, sodium chloride, or polyalcohols such as mannitol and sorbitol in the composition. Prolonged absorption of the injectable compositions can be brought about by including in the composition an agent which delays absorption, for example, aluminum monostearate or gelatin.

Sterile injectable solutions can be prepared by incorporating nattokinase in the required amount in an appropriate solvent with one or a combination of ingredients enumerated above, as required, followed by filtered sterilization. Generally, dispersions are prepared by incorporating nattokinase into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of nattokinase plus any desired ingredients from a previously sterile-filtered solution thereof.

The nattokinase for Alzheimer's disease, prion diseases and other central nervous system amyloidoses may be optimized to cross the blood-brain barrier. Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In one embodiment, nattokinase may be directly administered to the cerebrospinal fluid by intraventricular injection. In a specific embodiment, it may be desirable to administer nattokinase locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment nattokinase may be delivered in a controlled release system, such as an osmotic pump. In yet another embodiment, a controlled release system can be placed in proximity to the therapeutic target, i.e. the brain, thus requiring only a fraction of the systemic dose.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of dissolving or disrupting pre-formed or pre-deposited amyloid fibrils and/or inhibiting amyloid formation, deposition, accumulation, or persistence in an in vitro amyloid environment, the method comprising:
adding to the in vitro environment a composition comprising an effective amount of nattokinase.

2. The method of claim 1, wherein the amyloid is associated with Alzheimer's disease and/or a prion disease.

3. The method of claim 1, wherein the amyloid is associated with a prion disease.

4. The method of claim 1, wherein the in vitro environment comprises an object selected from the group consisting of a medical device, a pharmaceutical product, and an animal feed.

5. The method of claim 4, wherein the medical device is selected from the group consisting of a surgical instrument and a hemodialysis tubing.

6. The method of claim 4, wherein the pharmaceutical product is a blood product.

7. A method of catalyzing the degradation of amyloid fibrils comprising contacting in vitro amyloid fibrils with a composition comprising nattokinase in an amount effective to degrade the amyloid fibrils.

8. The method of claim 7, wherein the amyloid fibrils are selected from the group consisting of Aβ amyloid fibrils, prion fibrils, insulin fibrils, transthyretin fibrils, β-microglobulin fibrils, and any combination thereof.

9. The method of claim 7, wherein the contacting step is performed on an object susceptible to contamination by prion protein.

10. The method of claim 9, wherein the object is selected from the group consisting of a medical device, a pharmaceutical product, and an animal feed.

* * * * *

SEQUENCE LISTING

```
<160> NUMBER OF SEQ ID NOS: 2

<210> SEQ ID NO 1
<211> LENGTH: 40
<212> TYPE: PRT
<213> ORGANISM: Artificial Sequence
<220> FEATURE:
<223> OTHER INFORMATION: Peptide Abeta 40

<400> SEQUENCE: 1

Asp Ala Glu Phe Arg His Asp Ser Gly Tyr Glu Val His His Gln Lys
1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 37
<212> TYPE: PRT
<213> ORGANISM: Artificial Sequence
<220> FEATURE:
<223> OTHER INFORMATION: human prion peptide sequence 108-144 with Val
      at residue 129 (huPr)

<400> SEQUENCE: 2

Asn Met Lys His Met Ala Gly Ala Ala Ala Ala Gly Ala Val Val Gly
1               5                  10                  15

Gly Leu Gly Gly Tyr Val Leu Gly Ser Ala Met Ser Arg Pro Ile Ile
            20                  25                  30

His Phe Gly Ser Asp
        35
```